United States Patent
Reimels et al.

(10) Patent No.: US 8,083,781 B2
(45) Date of Patent: Dec. 27, 2011

(54) BONE PLATE SYSTEM PROVIDING DYNAMIC COMPRESSION

(76) Inventors: William J. Reimels, Goleta, CA (US); Bradford H. Hack, La Canada, CA (US)

(*) Notice: Subject to any disclaimer, the term of this patent is extended or adjusted under 35 U.S.C. 154(b) by 858 days.

(21) Appl. No.: 11/561,095

(22) Filed: Nov. 17, 2006

(65) Prior Publication Data
US 2007/0293864 A1    Dec. 20, 2007

(51) Int. Cl.
*A61B 17/66* (2006.01)
(52) U.S. Cl. ...................................................... 606/282
(58) Field of Classification Search .................. 606/280, 606/257, 282
See application file for complete search history.

(56) References Cited

U.S. PATENT DOCUMENTS

| | | | | |
|---|---|---|---|---|
| 5,458,642 A * | 10/1995 | Beer et al. | ................... | 623/17.13 |
| 5,797,912 A * | 8/1998 | Runciman et al. | ............. | 606/286 |
| 6,682,530 B2 * | 1/2004 | Dixon et al. | .................... | 606/279 |
| 2005/0043732 A1 * | 2/2005 | Dalton | ............................. | 606/61 |
| 2005/0192581 A1 * | 9/2005 | Molz et al. | ........................ | 606/74 |
| 2005/0203519 A1 * | 9/2005 | Harms et al. | ..................... | 606/61 |
| 2006/0235405 A1 * | 10/2006 | Hawkes | .......................... | 606/69 |
| 2006/0264937 A1 * | 11/2006 | White | .............................. | 606/61 |
| 2006/0264941 A1 * | 11/2006 | Lins | ................................ | 606/61 |

OTHER PUBLICATIONS

Sarin et al. (A Novel Iso-Elastic Cerclage Cable for Treatment of Fractures). Kinamed, Inc. Poster presented at 2005 Orthopedic Research Society (held Feb. 20-23, 2005).*
Sarin et al. (Novel Iso-Elastic Cerclage Cable for Fracture Treatment). Kinamed Inc. Dated Sep. 23-25, 2004, Rome, Italy. Journal of Bone and Joint Surgery—British Volume. vol. 90-B. Issue SUPP_I, 189. International Society for Technology in Arthroplasty.*

* cited by examiner

*Primary Examiner* — Thomas C. Barrett
*Assistant Examiner* — David Bates
(74) *Attorney, Agent, or Firm* — Laura Tunnell

(57) ABSTRACT

An orthopedic bone plate, suitable for internally fixating and stabilizing fractured bones, includes: an elongated structure, capable of contraction in a longitudinal direction and having at least two ends, the structure having at least two fixation points adapted to be fixated to a fractured bone with the fixation points on opposing sides of a fracture. An elastic, polymer cable is longitudinally stretched and coupled in tension to the elongated structure, capable of causing the structure to contract in the longitudinal direction.

14 Claims, 6 Drawing Sheets

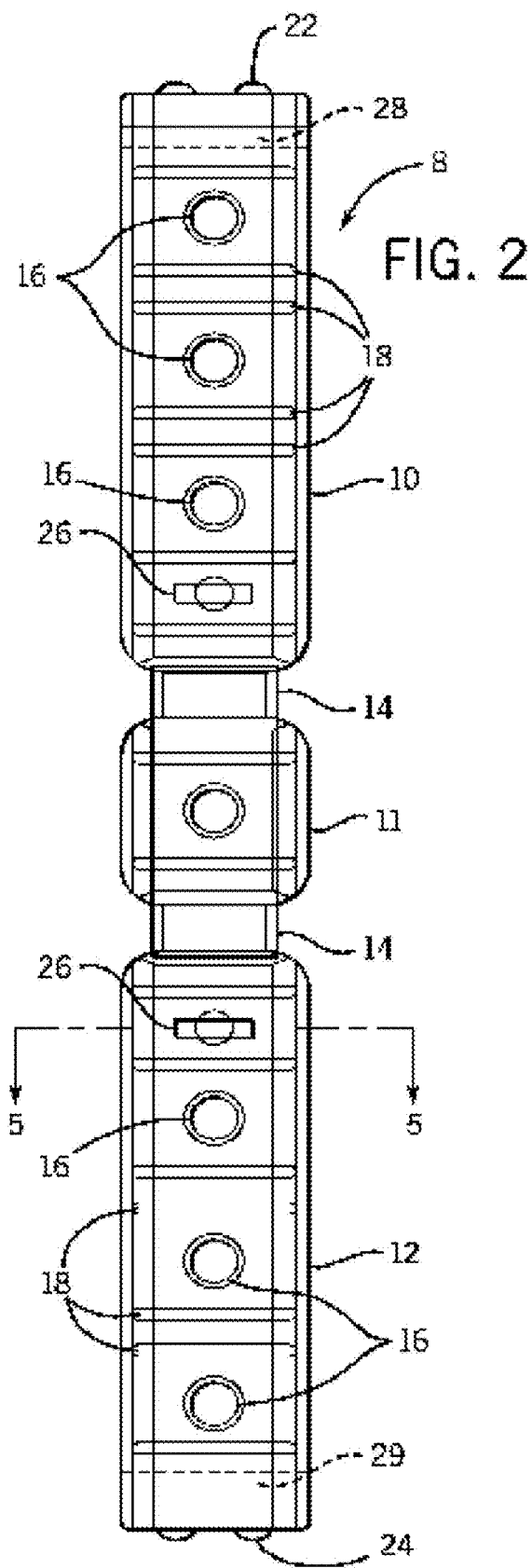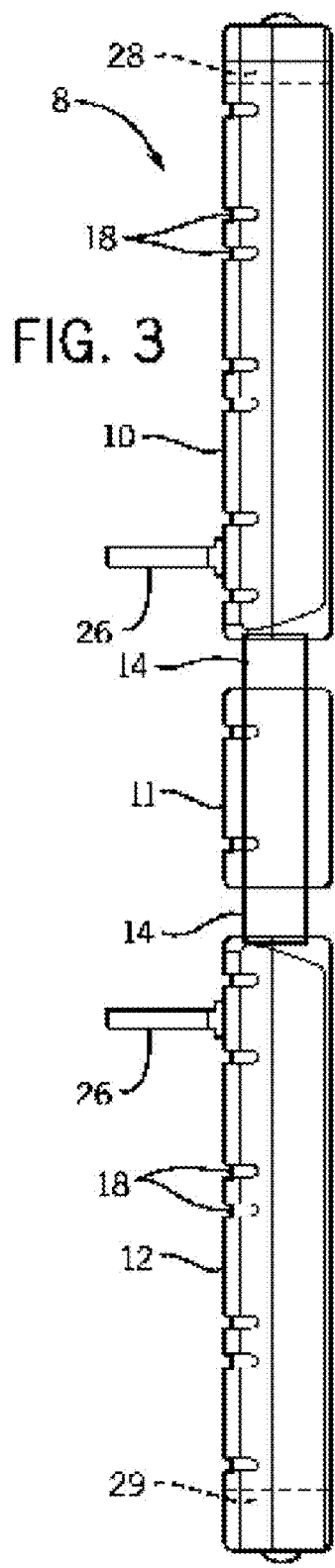

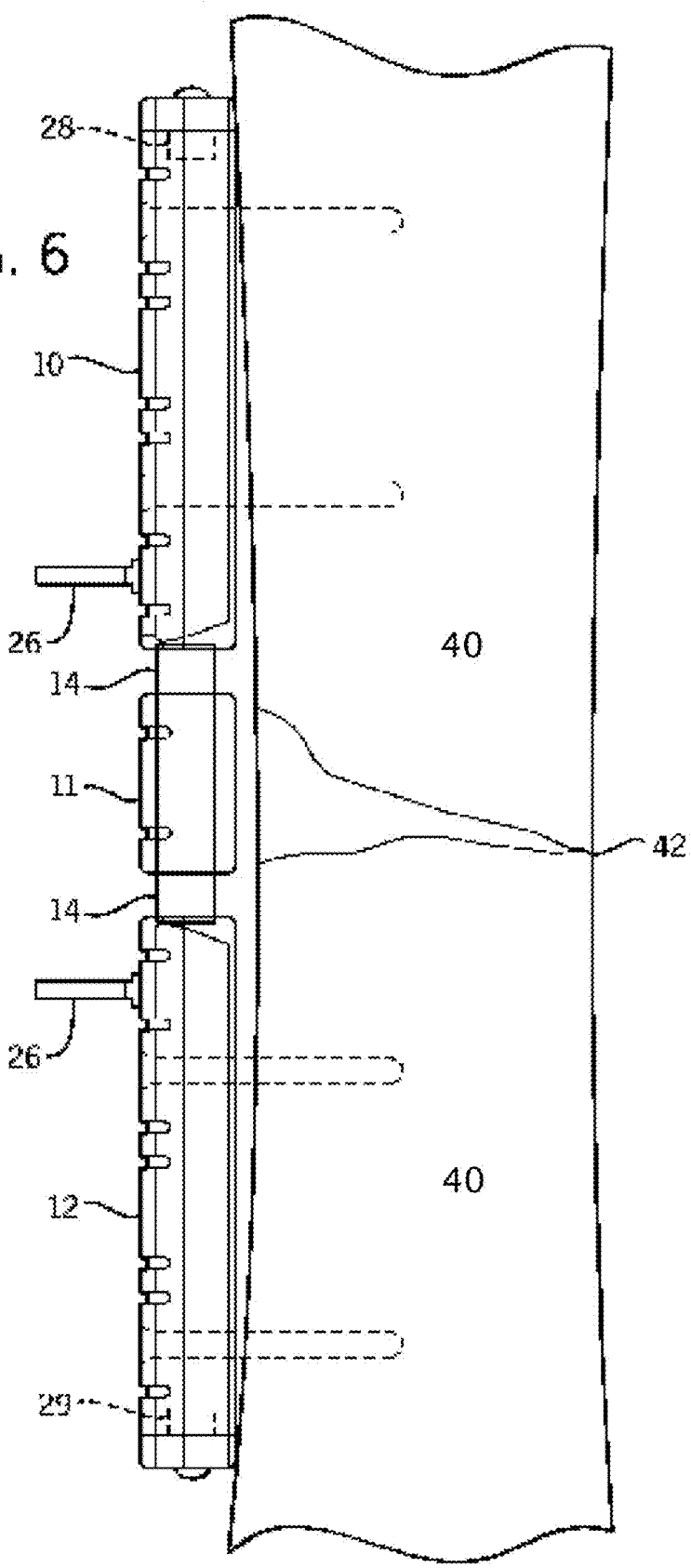

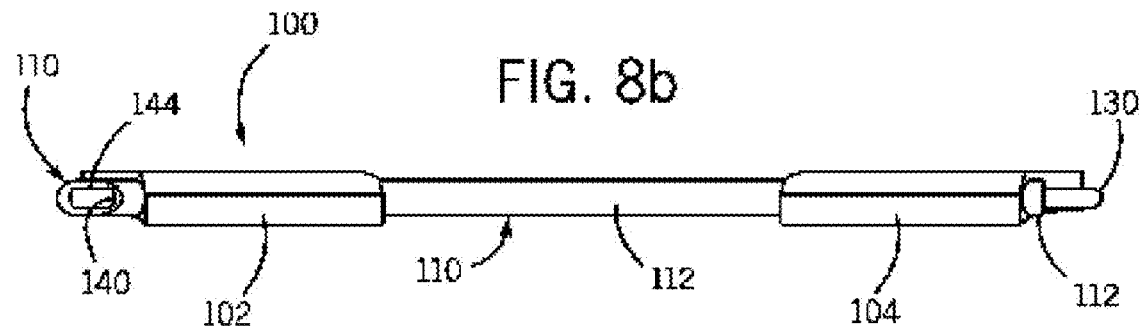
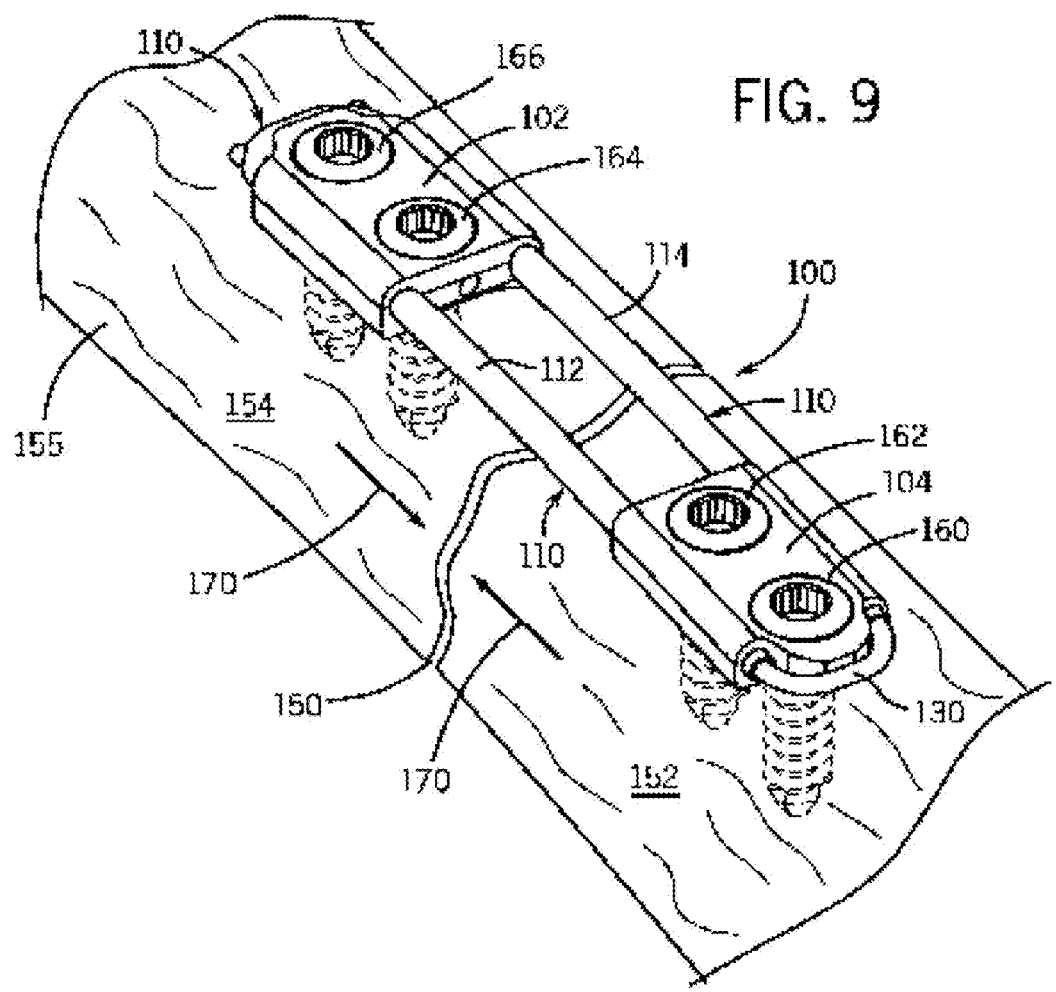

BONE PLATE SYSTEM PROVIDING DYNAMIC COMPRESSION

CROSS REFERENCE TO RELATED APPLICATIONS

This application claims the benefit of U.S. patent application Ser. No. 11/454,344 filed on Jun. 16, 2006, which is incorporated herein by reference.

BACKGROUND OF THE INVENTION

1. Field of the Invention

This invention relates to surgical devices generally and more specifically to orthopedic bone plates suitable for internally fixating and stabilizing fractured bones.

2. Description of the Related Art

Many bony fractures require stabilization that cannot be provided by external splints or casts; internal fixation is therefore required. Bone plates are among the most common artificial orthopedic implants, and are commonly used to stabilize and internally fixate bony fractures.

A conventional bone plate is essentially a rigid metal plate drilled with guide holes through which bone screws can be passed. Bone screws are usually inserted through the mounting holes and threaded into the bone above and below the fracture to fix the bone plate, thereby stabilizing and fixating the fracture. Often the bone plate is removed after healing has occurred (although not necessarily).

More recently, physicians have given increasing emphasis on bone plates and devices which are capable of providing compression of the fracture as well as stabilization. Most conventional compression plates are made of metal materials having modulus much higher than that of bone. Use of such plates produces a mechanical system in which the majority of the stress is borne by the plate rather than the bone, a situation sometime referred to as "stress-shielding." This situation is deleterious even to healthy, uncompromised bone, and can seriously impair the healing process in a fractured bone. Furthermore, it is now known that a controlled compressive load should be maintained across a fracture to promote rapid healing. Conventional, static bone plates do not provide or maintain such conditions.

Some bone plates include provision for introducing compression across the fracture when setting the plate. Usually the method of producing compression relies on an unusual bone screw or an unusual relationship between the screw and the mounting holes. Such methods can introduce initial compression, but the compression is difficult to maintain. Small movements of the bone interact with the typically high-modulus metallic plate, causing large fluctuations of the compressive load. Furthermore, some resorption may occur as a prelude to osteosynthetic growth, resulting in contraction of the bone in the region of the fracture. Even small contractions will produce slack sufficient to leave the fracture without compression (because the high-modulus metal plate cannot accommodate the contraction).

Alternatives to metal materials have been explored by some, including bioabsorbable materials and synthetic composite materials. Such materials appear promising, but offer their own challenges. There are still unanswered questions concerning the biocompatibility, strength, stability, reliability, wear, and ease of manufacture and handling. Most physicians continue to prefer metal plates to synthetic, for these reasons.

SUMMARY OF THE INVENTION

In view of the above problems, the present invention is an orthopedic bone plate system or bone bridge, suitable for internally fixating and stabilizing fractured bones, comprising: an elongated structure, capable of contraction in a longitudinal direction and having at least two ends, the structure having at least two fixation points adapted to be fixated to a fractured bone with the fixation points on opposing sides of a fracture. An elastic, polymer cable is longitudinally stretched and coupled in tension to the elongated structure, capable of causing the structure to contract in the longitudinal direction.

These and other features and advantages of the invention will be apparent to those skilled in the art from the following detailed description of preferred embodiments, taken together with the accompanying drawings, in which:

BRIEF DESCRIPTION OF THE DRAWINGS

FIG. 2 is a plan view from above of an apparatus representing a first embodiment in accordance with the invention;

FIG. 3 is an elevation view of the apparatus of FIG. 1;

FIG. 6 is a side view of the apparatus of the invention in relation to a fractured bone, showing how the apparatus may be employed in a method of fixing a fractured bone;

FIGS. 8a, 8b and 8c are a plan view, side view and cross-sectional view, respectively, of the apparatus of FIG. 7 (8c being cross-sectional along lines 8c-8c in FIG. 8a) in accordance with the invention.

FIG. 9 is an elevated perspective view of the apparatus of FIG. 7 surgically installed across a bone fracture and in operation in accordance with the invention.

DETAILED DESCRIPTION OF THE INVENTION

Figure 1:
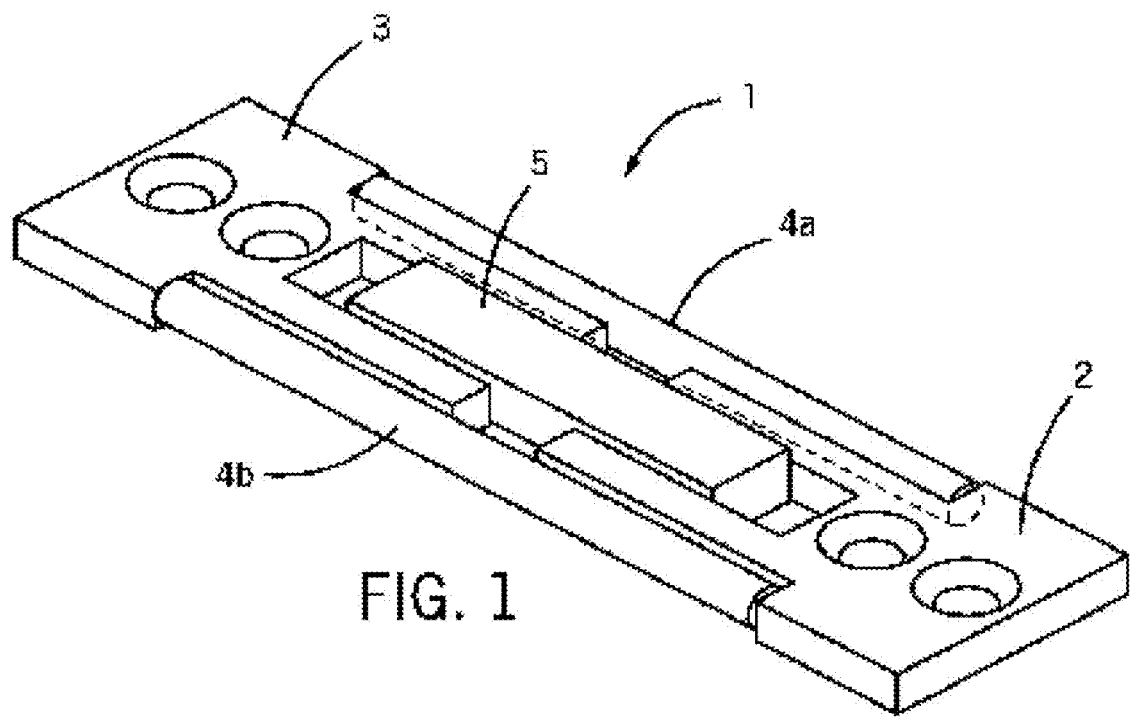
FIG. 1 is an elevated perspective view of a generalized construction of the bone bridge apparatus of the present invention.

Referring now to FIG. 1, as generally described, the apparatus of the invention includes a contractible, stabilizing structure 1 adapted to contract longitudinally in response to an elastic, polymer cable in sustainable tension. The structure 1 is adapted to be fixed to a bone at least at two points or bone plates 2 and 3 on opposing sides of a bone fracture. The plates 2 and 3 are then urged toward one another under elastic tension applied to the structure by an elastomeric (elastic polymer) cable component 4a and 4b, tending to compress the interposed bone fracture. The plates 2 and 3 are guided to move or slide with a single degree of freedom in a longitudinal direction by a guide structure 5 coupled to the plates 2 and 3. Preferably, the elastomeric cable is adapted to maintain a predetermined compression in a predetermined range across the fracture, notwithstanding any contraction or expansion of up to several millimeters, as set forth more particularly below.

In some embodiments the bone plate system of the invention also includes a locking mechanism for locking the bone plates in a pre-tensioned, extended position. In the locked position the fixation points are retained in an extended, pre-tensioned position before and during fixation to the fractured bone. After fixation to the bone with fixation points disposed on opposing sides of the fracture, the locking mechanism is released, causing the pre-set tension to be transferred to the bone, tending to compress the fracture by a pre-determined force generally linearly increasing with separation of the bone plates but controlled to only change by limited amounts over the operative range of motion of the apparatus, as hereinafter described in greater detail with respect to FIG. 10. The bone and bone plate thus become a mechanical system in equilibrium: in the longitudinal direction the bone plate, under tension from the elastomeric cable, supplies tension which is countered by equal longitudinal compression of the bone across the fracture. Though capable of contraction in the longitudinal dimension, the bone plate is generally rigid in transverse, shear, and torque directions to stabilize and splint the fracture during healing.

FIG. 2 shows generally at 8 a particular first embodiment of a bone plate system in accordance with the invention. The embodiment includes three slidable members, 10, 11 and 12, slidably mounted on a rail 14. Although three slidable members are shown, this number is not intended as a limitation, but merely as an illustration. In most embodiments, at least two such members should be provided; more may be used. In some embodiments, the invention could include only a single slidable member on a rail, with the rail adapted for fixation to the bone. Alternatively, two slidable rails coupled together telescopically could be used, both rails adapted for fixation to the bone at fixation points. The significant relationship is that at least two points of fixation are provided, capable of elastically loaded displacement in relation to each other in a longitudinal direction.

The stabilizing structure comprising the slidable members 10-12 and rail 14 preferably provides structural stability in at least two degrees of freedom: specifically, the structure should be substantially rigid with respect to bending moment and torque about the longitudinal axis of the structure. These qualities permit the structure to splint a fracture much like a conventional bone plate. However, unlike conventional bone plates, the bone plate of the invention is capable of more significant contraction (or in some embodiments, expansion) in the longitudinal direction.

Two species of exemplary features are illustrated for fixing the slidable members (10, 11, 12) to a fractured bone. Referring to FIGS. 2-6, holes 16 through members 10 and 12 are suitably provided with diameter sufficient to pass a shaft (but not a head) of a bone screw. Thus, bone screws may be passed transversely through the holes and threaded into a bone below the holes, thus fixing the slidable members 10 and 12 to a (fractured) bone at two points disposed on opposing sides of a fracture. Alternatively, transverse grooves or slots 18 can be used and are also shown. These allow the bone plate to be fixed by looping cable (cerclage) circumferentially around the bone and plate, with the cable seating in the groove or slots 18. The cable (not shown) is then tightened to grip the bone and plate in the manner of a lashing. Either the cerclage-cable, bone screws, or other means of fixation may be used either alternatively or in combination, without departing from the scope of the invention.

Figure 4:
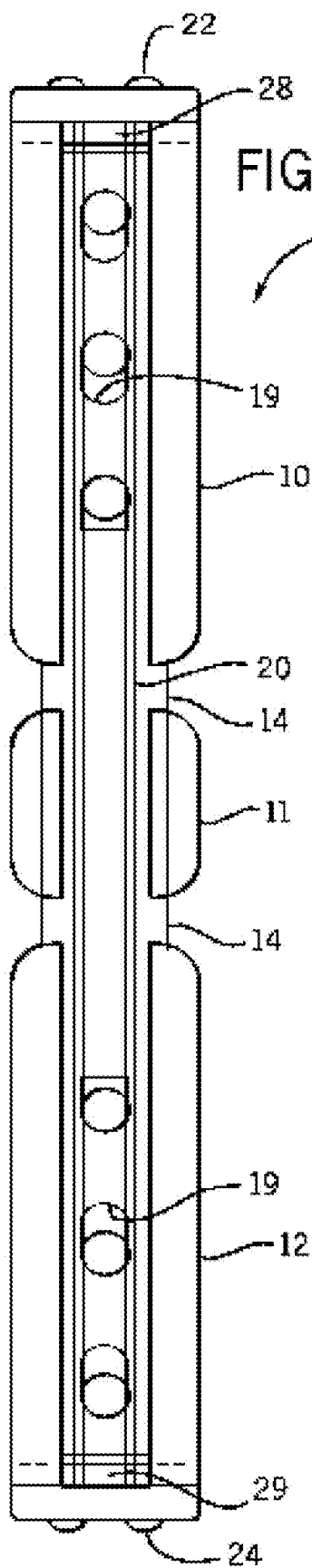
FIG. 4 is a plan view from below of the apparatus of FIGS. 1 and 2.

The underside view (FIG. 4) shows slots 19 in rail 14, generally aligned with the holes 16 in the slidable members 10 and 12. The slots allow passage of bone screws in an embodiment adapted for fixation by bone screws; the length of the slots should be sufficient to accommodate the desired contraction and/or expansion of the contractible structure during healing. For example, in one embodiment enough slot length should be provided to permit 1 to 5 millimeters of contraction or expansion. FIG. 4 also shows that one or more run or runs of an elastomeric cable 20 are fixed in tension at opposite ends between opposite slidable members 10 and 12. The cable runs longitudinally and internally through the rail, between the slidable members 10 and 12. Cable ends are fixed and anchor points 22 and 24 on the slidable members. In some embodiments, the length of available cable is pre-determined before delivery of the system. More particularly, in some embodiments the bone plate is supplied in an extended position with the cable pre-tensioned to a desired tension. In such embodiments the separation of the slidable members (and hence the tension in the cable) is maintained by at least one locking mechanism 26 which releasably hinders contraction of the device until the locking mechanism is released by a surgeon. Details of the locking mechanism 26 are discussed below, in connection with FIG. 5.

Elastomeric bumpers 28 and 29 are optionally positioned on one or more of the slidable members, capable of contacting the rail 14. These bumpers optionally act as limits or "stops" to the longitudinal contraction of the stabilizing structure. In many applications it may be desired to limit the potential for contraction of the device. If the device is pre-tensioned and locked with a known clearance between the bumpers 28 and 29 and the ends of rail 14, then the maximum contraction will be limited by the clearance. Once the clearance is taken up, the elastomeric bumpers 28 and 29 provide for a controlled release of compressive force as the ends of rail 14 contact the bumpers and limit contraction.

A cable suitable for use as elastomeric cable 20 in the invention should have at least two qualities: a) relatively high breaking strength, in the range at least 200 and preferably 400 lbs for a cable of 1-2 mm in diameter, and b) the ability to maintain the tension within a desired range notwithstanding substantial displacement (plus or minus) of the fracture. It is known that fractures may slightly contract due to resorption prior to healing, which may create shortening of the bone of up to of several millimeters. It is also known that living bone under changing loads flexes, extending and contracting in response to load. For this reason, to maintain proper compression on the fracture the cable in the invention should preferably possess specific force/extension characteristics at the working tension (in the 50-450 Newton range). We can define an axial modulus parameter Q as the cable tension (in Newtons) multiplied by the cable's static (unloaded) length, divided by the quantity working length minus unloaded length. For preferred embodiment, this axial modulus Q should preferably be below 1400 (Newtons), and more preferably in the Range of 160 to 1800 Newtons. Higher values impose difficulties in accurately imposing and maintaining tension, based on the precision of the assumed cable take-up mechanism. In other words, Q values below 1800 are preferred so that the working elongation is a manageable displacement at the working tension Preferably, the cable's force/extension characteristic should be relatively linear in the working region. Weaker elastomeric cables (such as urethane monofilament) are capable of significant contraction/extension while maintaining substantially constant tension; but such cables are not suitable because they exert insufficient working tension. On the other hand, metal alloy cables exert significant tension but do not maintain the working tension within a zone of tolerance if stretched or slackened by millimeters. Metal cables cannot stretch over the load ranges required, primarily because of their high elastic modulus.

The strength and extension characteristics discussed above should also be understood in the context of working lengths and diameters suitable for use in a bone plate. Suitable cable diameters for this application would be in the 1.0-2.0 millimeter range; working lengths are typically in the 10-30 cm range, constrained by the length of the bone plate apparatus.

Suitable cable preferably should also allow substantial elongation without danger of failure. For this reason the cable should preferably be capable of extension by a substantial percentage, preferably 50 and more preferably at least 100 percent, without significant risk of failure. Furthermore, it will be apparent that bio-compatible materials should be employed, more specifically, bio-compatible materials that can be suitably sterilized and preferably packaged in hermetically sealed packaging for distribution.

The inventors have found that a suitable cable can be engineered as at least relatively lower strength, monofilament polymer core (for example, nylon, silicone or urethane core) surrounded by a woven, relatively higher strength polymer jacket woven from ultra-high molecular weight polyethylene fibers. The jacket fibers significantly increase the strength, reliability, and maximum extension before failure of the cable.

Figure 5:
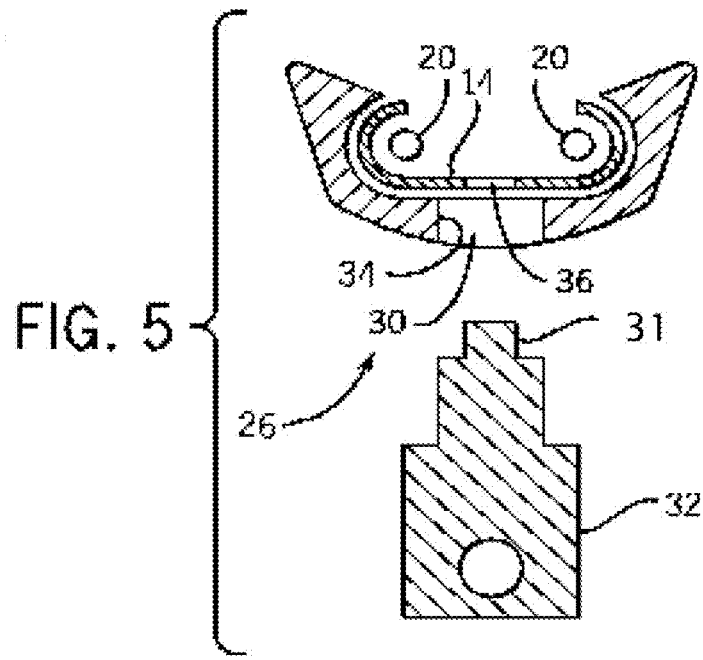
FIG. 5 is a partially exploded, cross sectional view, taken along section line 4 of FIG. 1, showing details of a locking mechanism.

The expanded, cross-sectional view of FIG. 5 shows details of a locking mechanism, suitable for use in a pre-loaded embodiment of the bone plate. The slidable member 10 can be seen to partially surround the rail 14, with a slidable fit between the parts. Transverse to the axis of the rail, a slot, hole or notch 30 is provided in the rail 14, capable of receiving a matching tab or tongue 31 of a key 32. The wall of said notch 30 is indicated at 34. A second notch, hole or slot 36 is also provided in the slidable member 10. For locking, slots, holes or notches 30 and 36 are aligned with the cable 20 set to the desired, pre-determined tension; then the key 32 is inserted, transfixing the assembly of rail 14, slidable member 10 and key 32. The key is retained because the tension in cable 20 is transferred to a shearing compression across the tongue 30 of key 32. In this position, the bone plate may be retained in a pre-loaded, tensioned and expanded configuration until the key 32 is withdrawn.

Variant, more or less complex locking mechanisms, including pins and screws, might be employed without departing from the invention.

A method of fixing a fracture in accordance with the invention can be visualized by reference to FIG. 6. The bone plate system or bone bridge (generally at 8) is shown in relation to a long bone 40, with a fracture at 42. We assume that the bone plate system is pre-tensioned and locked as described above; otherwise, the device should be pre-tensioned and locked as a preliminary step. To internally fix the fracture, the fracture is first reduced (typically during open surgery). The surgeon then places the bone plate adjacent to the bone, across the fracture in a splint-like configuration, with the longitudinal axis (defined by the permitted direction of contraction of the bone plate) across the fracture.

Once positioned, the bone plate is fixed to the bone by fixing opposing slidable members 10 and 12 to the bone on opposite sides of the fracture 42. Optionally, a further slidable member (or multiple members) may be positioned to further support and stabilize the fracture, as shown. As previously discussed, the slidable members may be fixed, for example, by placement of bone screws passed through the fixation holes 16. Alternatively, or in addition, cerclage may be wrapped around the bone and engaged in the slots.

After the slidable members are fixed on opposite sides of the fracture, one or both of the keys 32 are removed. With the keys removed, there is no obstacle (other than the bone) to contraction of the slidable members toward one another. The bone plate tends to contract under the tension of the cable 20, drawing the slidable members toward one another and compressing the fracture by a predetermined and controlled load. The keys are then discarded by a method proper for medical waste.

Figure 7:
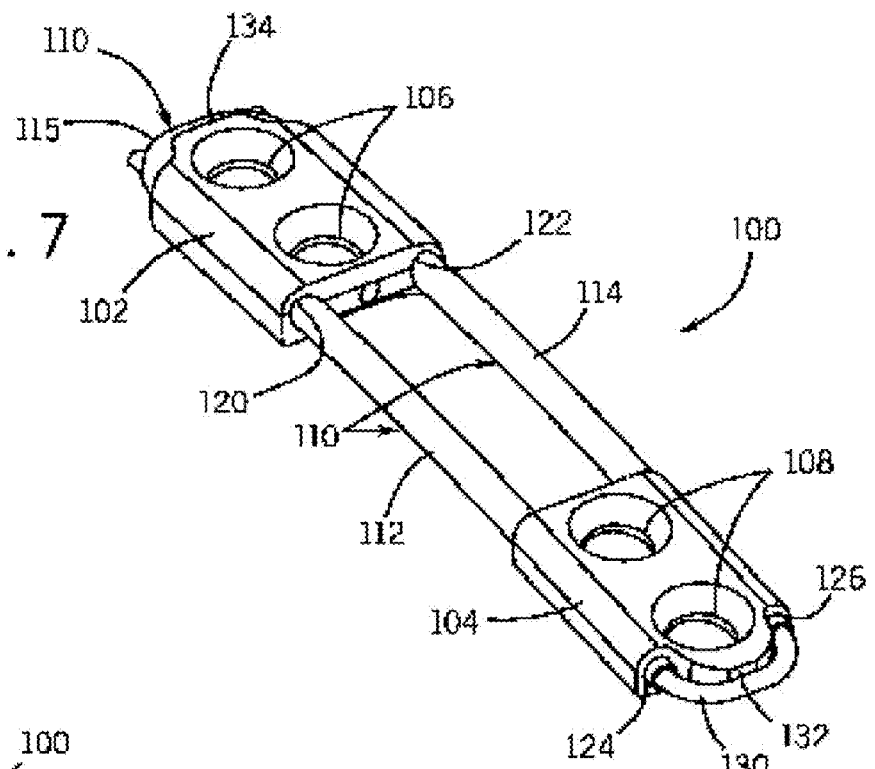
FIG. 7 is an elevated perspective view of an apparatus representing a second embodiment in accordance with the invention.

FIG. 7 shows generally a particular second embodiment of a bone plate system or bone bridge 100 in accordance with the invention in a relaxed state. The embodiment includes a first fixed bone plate 102 and a second movable bone plate 104 each of which has a set of countersunk holes or apertures 106 and 108 through which bone screws or other fasteners may extend to individually affix the plates 102 and 104 to different bone fragments on different sides of a bone fracture. A hollow U-shaped cylindrical tube 110 has a 180 degree reverse bend 115 at its proximal end and defines two parallel spaced-apart legs 112 and 114 open at their distal ends. The plates 102 and 104 and the U-shaped tube 110 are preferably fabricated from stainless steel or titanium. The legs 112 and 114 extend through the plates 102 and 104 in cylindrical channels or passages 120 and 122 in plate 102 and cylindrical channels or passages 124 and 126 in plate 104. The passages 120, 122, 124 and 126 are of a slightly larger inside diameter than the outside diameter of the legs 112 and 114 and therefore the plates 102 and 104 are free to slide up and down along the legs 112 and 114 of the tube 110, subject to retention at the far ends of the tube 110 as further described below. An elastic polymer cable or microcable 130 extends around the curved outer end 132 of the plate 104 and extends down the interior of the legs 112 and 114 from the distal end (open end) of the U-shaped tube 110 to the proximal end of the tube 110 (closed end, at the bend 115) toward the curved outer end 134 of the plate 102. The elastic polymer microcable 130 preferably comprises a relatively lower strength, elastic polymer core, such as nylon, clad in a relatively stronger woven jacket, said woven jacket including ultra-high molecular weight polyethylene fibers. The ends of the elastic microcable 130 are secured within the tube 110 by being crimped in place in proximity to the proximal end of the tube 110 at the working position of the fixed plate 102 which operationally attaches the ends of the microcable 130 to the plate 102. In use the microcable 130 stretches allowing the movable plate 104 to slide along the legs 112 and 114 away from the fixed plate 102 under controlled tension provided by the elastic microcable 130 which continuously engages the movable plate 104. The tensile force provided by the elastic microcable 130 is applied as a compressive force on a bone fracture that promotes healing when the bone plates 102 and 104 are secured to opposing bone fragments and deployed across a bone fracture and the plates 102 and 104 are suitably spaced apart.

Figure 8A:
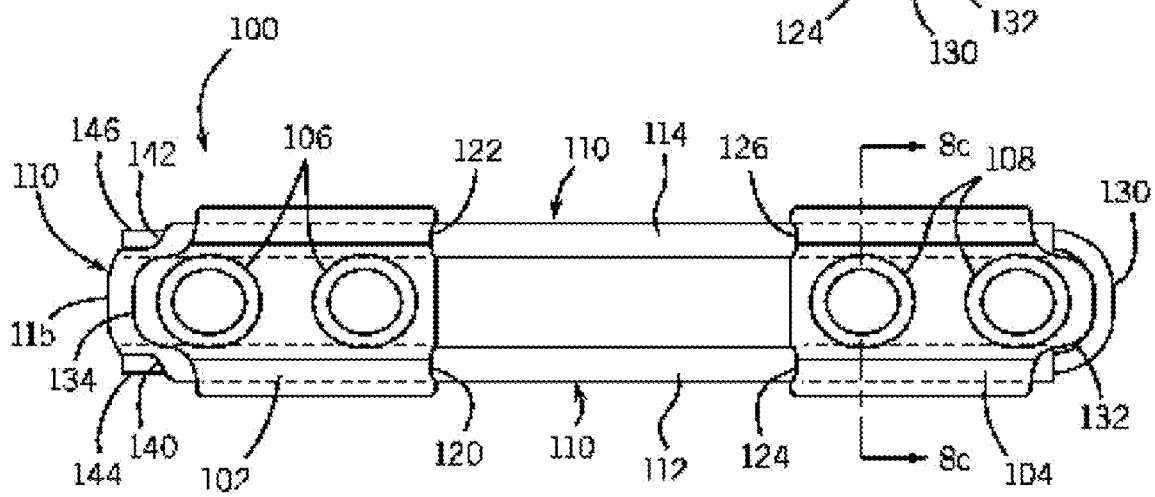
Figure 8C:
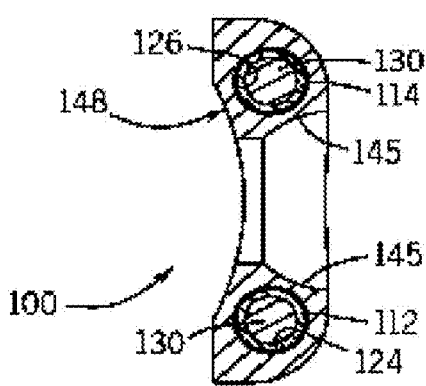

FIGS. 8a-8c generally show different views of the bone plate system or bone bridge 100 in accordance with the invention again in a relaxed state. FIGS. 8a and 8b illustrate how the tube 110 wraps around the curved outer end 134 of the fixed plate 102 at its bend 115 while the microcable 130 correspondingly wraps around the curved outer end 132 of the movable plate 104. The legs 112 and 114 of the U-shaped tube 110 run through the matching passages 120 and 122, and 124 and 126 that are disposed on opposite transverse sides of the plates 102 and 104 allowing the plates to be slidably engaged on the legs of the tube 110. The apertures 106 and 108 are centrally positioned on the plates 102 and 104 to allow bone screws or the like to be properly secured at the apertures into bone fragments in order to affix the plates 102 and 104 to different bone fragments spanning a bone fracture. FIGS. 8a and 8b also show holes 140 and 142 in the tube 110 at opposite sides of the bend 115 that are in line with the legs 112 and 114. The holes 140 and 142 allow the ends 144 and 146 of the microcable 130 to extend out of the proximal end of the tube 110 during assembly so that the full passage of the microcable down the legs 112 and 114 can be visually confirmed prior to their being crimped in place and the cable ends being trimmed off. FIG. 8c shows the legs 112 and 114 of the tube passing through the passages 124 and 126 in the plate 104, depicts the countersink 145 of one of the apertures 108 and illustrates the transverse concave configuration 148 of the bone bridge which allows for easier centering on generally convex bone surfaces.

FIG. 9 shows the second embodiment of a bone plate system or bone bridge 100 in accordance with the invention surgically installed across a bone fracture 150. The bone bridge 100 is in a tensioned state following the plates 102 and 104 being spaced apart at a fixed distance to provide a controlled amount of compression, held in position during surgical installation and subsequently released to allow compressive force to be applied to a fracture. The bone screws 160 and 162 are installed to anchor the movable plate 104 onto the bone fragment 152. The bone screw 162 and 164 are installed to anchor the fixed plate 102 onto the opposing bone fragment 154. The microcable 130 is engaged with and around the movable plate 104 while the tube 110 is engaged with and around the fixed plate 102. The plates 102 and 104 are spaced apart along the legs 112 and 114 with the microcable in tension pulling the plates toward each other and correspondingly furnishing the compressive force illustrated by arrows 170 on the fracture 150.

Figure 10:
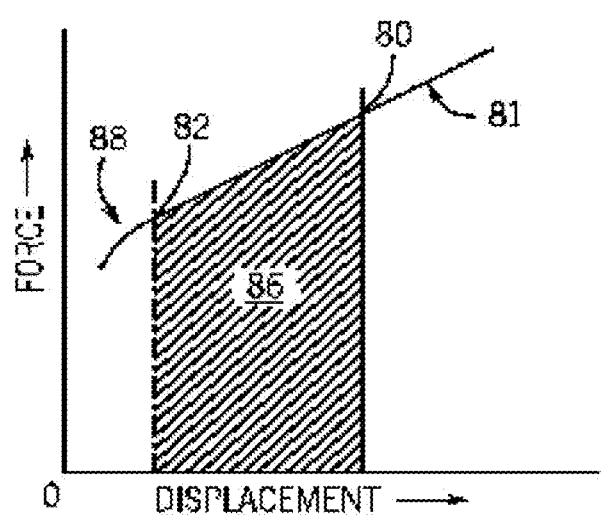
FIG. 10 is a graph of force as a function of extension for a bone plate in accordance with the invention, illustrating elastic and energy storage characteristics.

The graph of FIG. 10 illustrates force vs. displacement and energy storage in the apparatus of the invention. The force as a function of displacement is substantially linear with a limited rate of change (slope) in a significant region of the graph. In preferred embodiment, the invention is pre-tensioned or biased at a point 80 on curve 81, calculated to be in a substantially linear region of the curve 81 by the elastic microcable. The bias point 80 is predetermined to allow room for contraction and/or expansion without either a) breaking the cable, or b) incurring excessively low or excessively high tension. The bias point of the cable in the invention departs from prior bone plates, which have useful active ranges of only tenths of a millimeter due to the extremely high modulus of the solid metal parts as previously used.

The graph of FIG. 10 also illustrates energy storage in the apparatus of the invention, which is an alternate way of viewing or describing the action of the apparatus. The total area under the curve 81 represents the energy stored in the apparatus of the invention (primarily in the elastomeric cable) with the tension set at the predetermined bias point. The apparatus can contract to the limit 82, performing work equal to the hatched area 86 (part of the total area under 81).

In a typical embodiment such as for example the embodiment shown in FIGS. 2-6, the bias point is set at a point such that the pre-loaded apparatus stores energy of at least 0.1 Joules. More preferably, the preloaded apparatus stores energy of at least 0.5 Joules, more specifically in the range 0.5 to 10 Joules. This energy storage is believed to provide significant advantage over the relatively low energy storage of prior cables.

FIG. 10 also shows that the elastic curve of the device has a corner, and rolls off rapidly at lower extensions (region 88) as, for example, the rails contact the elastomeric bumpers 28 and 29 in the first embodiment shown, limiting the range of contraction.

The energy storage capacity of the invention provides advantage in at least two ways: the bone plate better accommodates contraction and expansion during healing, and the tension provides a dynamic load on the bone during healing, thereby preventing "stress shielding" and the resulting atrophy of bone which can occur with static metal bone plates.

While several illustrative embodiments of the invention have been shown and described, numerous variations and alternate embodiments will occur to those skilled in the art. One of the slidable members 10 or 12 could be integrated with the rail 14, allowing the second member to slide for contraction. Variants of the rail could be used, including telescoping rails, multiple rails, tongue and groove slots, dovetailed slots and tongue, or other telescoping or contractible mechanisms. The U-shaped tube 110 could have a different cross section such as being square or hexagonal. A single tube 110 could be employed in a manner similar to a rail with the microcable running down the tube but connected at opposite ends to opposing plates. Various types of holes and bone screws could be used, including slanted screws, oval holes, slots, and interfering arrangements of screws and slot as known in the art. The slidable members and/or rail could be contoured in cross section, and the contact points between the members and the bone could be varied. For example, minimal contact feet could be employed, or aggressive features such as teeth could be provided to grip the bone. Such variations and alternate embodiments are contemplated, and can be made without departing from the spirit and scope of the invention as defined in the appended claims.

We claim:

1. A bone bridge for use in stabilizing a bone fracture between two bone fragments, comprising:
    a first bone fragment plate having one or more mounting apertures for receiving one or more fasteners for attaching said first plate to a first bone fragment;
    a second bone fragment plate having one or more mounting apertures for receiving one or more fasteners for attaching said second plate to a second bone fragment;
    a guide structure for limiting the motion between said first and second bone plates to movement along a longitudinal axis defined by said bone fragments and linearly guiding the movement of said first bone plate with respect to said second bone plate; and
    an elastic polymer cable coupled to said first and second bone plates for generating a tensile force between said first and second bone plates along the longitudinal axis defined by said bone fragments in order to provide a compressive force between said bone fragments, wherein the elastic polymer cable is pre-tensioned such that an increase in the displacement between the first and second bone fragment plates requires a linear increase in the tensile force on the elastic polymer cable.

2. The bone bridge of claim 1, wherein:
    said elastic polymer cable comprises a relatively lower strength, elastic polymer core clad in a relatively stronger woven jacket, said woven jacket including ultrahigh molecular weight polyethylene fibers.

3. The bone bridge of claim 1, wherein:
    said guide structure for limiting the motion between said first and second bone plates comprises a first channel on said first plate and a second channel on said second plate and an elongate rail engaged with but capable of sliding within said channels.

4. The bone bridge of claim 3, wherein:
    said elastic polymer cable is attached to and extends between said plates within a recess defined by said rail in a state of controlled tension so as to be able to provide a compressive force on a bone fracture.

5. The bone bridge of claim 4, wherein:
    said elastic polymer cable comprises an relatively lower strength, elastic polymer core clad in a relatively stronger woven jacket, said woven jacket including ultrahigh molecular weight polyethylene fibers.

6. The bone bridge of claim 1, wherein:
said guide structure for limiting the motion between said first and second bone plates comprises a U-shaped hollow tube having a reverse bend which extends around and is secured to said first plate and having a pair of parallel hollow legs on which said second plate is slidably mounted.

7. The bone bridge of claim 6, wherein:
said elastic polymer cable extends inside hollow legs and around said second plate controlled tension so as to be able compressive force on a bone fracture.

8. The bone bridge of claim 7, wherein:
said elastic polymer cable comprises a relatively lower strength, elastic polymer core clad in a relatively stronger woven jacket, said woven jacket including ultrahigh molecular weight polyethylene fibers.

9. The bone bridge of claim 7, wherein:
said cable is secured to said first plate by being crimped into each of said legs at points adjacent to said bend in said tube and said first plate.

10. The bone bridge of claim 1, wherein:
said first and second bone fragment plates have a transverse concave configuration which enables easier centering on generally convex bone surfaces.

11. The bone bridge of claim 1, wherein:
said mounting apertures have countersinks and said fasteners are bone screws having hemispherical heads.

12. A bone bridge for use in stabilizing a bone facture between two bone fragments, comprising:
a first bone fragment plate having one or more mounting apertures for receiving one or more fasteners for attaching said first plate to a first bone fragment;
a second bone fragment plate having one or more mounting apertures for receiving one or more fasteners for attaching said second plate to a second bone fragment;
a guide structure including a elongate rail on which said plates are mounted that is adapted for mating with channels in said plates and for limiting the movement of said first bone plate with respect to said second bone plate along a single longitudinal axis defined by said bone fragments; and
an elastic cable coupled to said first and second plates for generating a tensile force between said first and second bone plates along the longitudinal axis defined by said bone fragments in order to provide and compressive force between said bone fragments, wherein the elastic polymer cable is pre-tensioned such that an increase in the displacement between the first and second bone fragment plates requires a linear increase in the tensile force on the elastic polymer cable.

13. The bone bridge of claim 12, wherein:
said elastic cable comprises a relatively lower strength, elastic nylon polymer core clad in a relatively stronger woven jacket, said woven jacket including ultra-high molecular weight polyethylene fibers.

14. The bone bridge of claim 12, wherein:
said elastic polymer cable is attached to and extends between said plates within a recess defined by said rail, and said mounting apertures have countersinks and said fasteners are bone screws having hemispherical heads.

* * * * *